United States Patent [19]
Dietl

[11] Patent Number: 5,637,317
[45] Date of Patent: Jun. 10, 1997

[54] PHARMACEUTICAL PREPARATION CONTAINING CYCLOSPORIN(S) FOR ORAL ADMINISTRATION AND PROCESS FOR PRODUCING SAME

[76] Inventor: Hans Dietl, Eichendorffstr. 33, Bad Aibling, Germany, D-83043

[21] Appl. No.: 610,820

[22] Filed: Mar. 8, 1996

Related U.S. Application Data

[60] Division of Ser. No. 335,298, Nov. 7, 1994, Pat. No. 5,529,785, which is a continuation-in-part of Ser. No. 60,654, May 12, 1993, Pat. No. 5,527,537.

[51] Int. Cl.$^6$ .............................. A61K 9/127; A61K 9/48; A61K 9/66; B01J 13/02
[52] U.S. Cl. ........................ 424/450; 424/451; 424/455; 436/829; 264/4.1
[58] Field of Search ................................ 424/450, 451, 424/455; 436/829; 264/4.1; 514/9, 11, 15

[56] References Cited

U.S. PATENT DOCUMENTS

| | | | |
|---|---|---|---|
| 4,388,307 | 6/1983 | Cavanak .................................. | 424/177 |
| 4,792,449 | 12/1988 | Ausman et al. ......................... | 424/440 |
| 5,206,219 | 4/1993 | Desai ...................................... | 424/455 |
| 5,294,604 | 3/1994 | Nussemblatt et al. .................. | 514/455 |

FOREIGN PATENT DOCUMENTS

| | | |
|---|---|---|
| 0 361 928 A2 | 4/1990 | European Pat. Off. . |
| 0 391 369 | 10/1990 | European Pat. Off. . |
| 43 15 921 A1 | 11/1993 | Germany . |

OTHER PUBLICATIONS

Y. Mizushima, "Lipid Microspheres As Novel Drug Carriers Drug Exptl Clinical Res X" 1(9), 1985 pp. 595–600.

A. Shah, et al. "Effect of Co–Administration of Intralipid . . . " Biopharmaceitocs & Drug Disp., vol. 12, 1991, pp. 457–466.

WPI/print out No. 86-335072, Mizushima, 1 pg, WPI print out No. 92-352740, Green Cross Corp., 1 pg.

A. Tibell, et al. Cyclosporins A in Fat Emulsion Carrier, Immuno Suppressive Effec in vitro, and J Immunolo. 35 pags, 231–236, 1992.

A. Yanagwa et al. "Selective transfer of cyclosporin to thoracic lymphatic systems . . . " J. Microncapsol, 1989, vol. 6, No. 2, pp. 161–164.

W. Homan et al, "Studies on Immuno Suppressive . . . " Transol., vol. 29, No. 5, pp. 361–366.

Chemical Patents Index, Derwent Publication LTD., London GB, Ref. AN 86–335072/51.

Chemical Patents Index, Derwent Publication LTD., London GB, Ref. AN 92–352740/43.

Chemical Abstracts. vol. 116, 1992, Ref. 158721j.
Chemical Abstracts. vol. 115, 1991, Ref. 197746v.
Chemical Abstracts. vol. 112, 1990, Ref. 204590h.
Chemical Abstracts. vol. 111, 1989, Ref. 12441t.
vol. 93, 1980, Ref. 37102f.

J. Pharm Sci, Ba 79, Nr 3, 1919, S. Venkataram; "Pharmacokinetics of two alternative dosage forms of cyclospoins: Liposomes and Intralipid".

Abstract No. 86–335071/51, Teikoku Hormone Mfg. Ltd., Japan, Apr. 26, 1985.

*Primary Examiner*—Carlos A. Azpuru
*Attorney, Agent, or Firm*—Townsend and Townsend and Crew LLP

[57] ABSTRACT

A cyclosporine(s)-containing pharmaceutical preparation for oral application is disclosed, comprising the following components:
- (a) at least one cyclosporine,
- (b) at least one natural oil of natural origin,
- (c) at least one member selected from the group consisting of 3-sn-phosphatidyl choline and phosphatidyl ethanol amine, and
- (d) water, with the proviso that ionic and non-ionic surfactants are excluded.

10 Claims, 1 Drawing Sheet

PHARMACEUTICAL PREPARATION CONTAINING CYCLOSPORIN(S) FOR ORAL ADMINISTRATION AND PROCESS FOR PRODUCING SAME

CROSS REFERENCE TO RELATED APPLICATION

This is a division of application Ser. No. 08/335,298 filed Nov. 7, 1994, now U.S. Pat. No. 5,529,785 which is a continuation-in-part of application Ser. No. 08/060,654, filed May 12, 1993, now U.S. Pat. No. 5,527,537.

The present invention relates to a new pharmaceutical preparation containing cyclosporin(s) for oral application, a process for producing this pharmaceutical preparation, as well as its application for oral administration.

BACKGROUND OF THE INVENTION

The present invention relates to a new pharmaceutical preparation containing cyclosporin(s) for oral application, a process for producing this pharmaceutical preparation, as well as its application for oral administration.

Cyclosporin(s) are cyclic oligopeptides from lower fungi, which were discovered by scientists at Sandoz AG, Basel. Cyclosporin A or Cyclosporin G, in particular, are used as immunosuppressant agents, specifically following organ transplant surgery. The cyclosporin derivative "SDZ IMM 125", a hydroxy ethyl derivative of D-serine-8-cyclosporin, is also preferred. The application in the case of other diseases, e.g., diabetes and psoriasis as well as numerous autoimmune disorders (e.g., rheumatoid arthritis, endogenous uveitis, etc.) has also been described.

Cyclosporin A is obtained as a white amorphous powder from fungi by means of column chromatography over silica gel; it crystallizes from acetone in the form of white needles having a melting point of 148° to 151° C. In addition to cyclosporin A, numerous other cyclosporins are known, ranging from cyclosporin A to cyclosporin Z (cf. Roempp's Chemie Lexikon, 9th edition, pages 841 to 843). Semisynthetic derivatives of cyclosporin are equally known and may be used in accordance with the invention. These are substances which are very similar to each other from a chemical point of view and which consist of cyclic polypeptides of 11, partially methylated, amino acids. Cyclosporins are soluble in alcohol, ether, acetone and chlorinated hydrocarbons and natural oils (triglycerides of fatty acids).

Cyclosporin A is commercially available for oral application in the form of capsules as well as a solution for administration per os. In both forms of administration the cyclosporin is dissolved in a mixture of ethanol with a vegetable oil (Pharmacopoeia Martindale, 29th edition, U.S. Pharm. XXII, 619, as well as the technical information SANDIMMUN® of the Sandoz company).

Moreover, further adjuvants other than ethanol and vegetable oil (preferably corn oil) are used to dissolve cyclosporin A and maintain it in dissolved form, such as poly(oxyethylene)-6-glycerol-tri-(oleate, linolate). The use of these adjuvants reveals the great problems involved in the administration of cyclosporin for oral administration in this form which ensures resorption at last in part.

The use of alcohol, which is always required, means a health risk for persons such as those suffering from liver diseases, alcoholics, epileptics, patients with cerebral disorders, and children. Moreover, the alcohol may reduce or increase the effects of other drugs administered simultaneously with cyclosporin.

The poly(oxyethylene)-6-glycerol-tri-oleates or linolates, which are used to achieve an improved solubility of the cyclosporins, may result in undesirable effects since they take an influence not only on cyclosporin resorption but also other substances such as fats, paraffins, vitamins, etc. Apart therefrom, the used quantities of these adjuvants should not exceed the level of 25 mg per kg of body weight. These substances may moreover induce undesirable allergic responses as intense as up to a physiological shock condition.

From a theoretical point of view it could also be possible to dissolve cyclosporin in pure vegetable oil for subsequent oral administration. In practice, however, this is not feasible because the patients are very reluctant to swallow pure oil and as resorption is not ensured.

The predominant problem involved in the aforedescribed forms of application of cyclosporin(s) for oral administration is, as a matter of fact, the poor and moreover strongly varying cyclosporin resorption. Resorption may be incomplete and varies strongly on an intra-patient basis; it may even be subject to intra-patient variations on a daily basis; in general it amounts to a level between 20 and 50% of the administered dose of cyclosporin(s). A uniform and homogeneous resorption would, however, be extremely desirable. Furthermore, it would be sensible to have cyclosporin preparations available which will globally ensure a better resorption, which means an improved biologic availability.

Even though the problems described here have been known for a long time attempts have so far been unsuccessful to find an optimum form for the oral administration of cyclosporin(s).

One object of the present invention therefore resides in the aspect to provide a pharmaceutical preparation containing cyclosporin(s), which will permit a better (increased) and more uniform resorption of cyclosporin(s) in administration per os. Intra- and inter-individual variations of cyclosporin levels in the blood are reduced.

Another object of the present invention consists in the provision of a pharmaceutical preparation for cyclosporin(s) for application, which does not contain any alcohol.

It is a further object of the present invention to dispense with additional adjuvants such as poly(oxyethylene)-40-castor oil as far as this is possible.

SUMMARY OF THE INVENTION

In accordance with the present invention these problems are solved by the fact that a pharmaceutical preparation containing cyclosporin(s) is made available which contains one or several cyclosporin(s), one or several natural oils, 3-sn-phosphatidyl choline and/or phosphatidyl ethanolamine and water in an oil-in-water emulsion, with (the) cyclosporin(s) being contained in the oily phase.

The present invention hence solves, in a surprising manner, the problem of the comparatively poor resorption and/or the resorption of cyclosporin(s) which varies strongly on an inter-patient basis, by the production of a preparation containing cyclosporin(s) for oral application, wherein the cyclosporin is contained in a therapeutically sufficient concentration in an oil-in-water emulsion consisting of natural triglycerides, 3-sn-phosphatidyl cholines and water.

The adjuvants ethanol and poly(oxyethylene) derivatives, which have so far been additionally used and which may be undesirable, may be contained in the inventive preparation, even though they are not definitely necessary.

In accordance with the present invention, the inventive preparation for oral application provides, in an entirely surprising manner, an improved and moreover more uniform, activity, i.e., an activity which may be dosed more precisely. Hence the cyclosporin dose may be reduced, with a corresponding reduction of the frequency and seriousness of the occurring side effects. Apart therefrom, if this appears to be necessary, it is possible to dispense with the additional application of ethanol and/or poly(oxyethylene) derivatives.

The improved and more uniform resorption of cyclosporin(s) is possibly achieved by the dissolution of cyclosporin in the microsphere of a fat particle in the inventive form of administration, and by the fact that this fat particle, with the cyclosporin contained therein, being decomposed and metabolized in the gastrointestinal tract in a manner in which this happens also to natural food such as milk.

Furthermore, the inventive pharmaceutical preparation permits a control of the rate of resorption of the cyclosporin (s). The fat particles in the emulsion, which contains the cyclosporin, may, as a matter of fact, be produced by varying the composition of the phosphatidyl choline in such a way that the cyclosporin is released rapidly or slowly. It is possible, for instance, to formulate the pharmaceutical preparation in a way that the fat particles are completely or partly decomposed in the stomach and release the cyclosporin(s) already in the stomach, or in a modified form such that the cyclosporin release occurs by far more slowly in the small intestine only while the pharmaceutical preparation as such passes through the stomach in unchanged form. A form of a pharmaceutical preparation is thus achieved which is fundamentally resistant to gastric juice.

These provisions ensure a considerable extension of the potential applications since they enable the cyclosporin release also as late as in the intestines, so that a form of administration is achieved which is in analogy with the physiologic processes of digestion.

DETAILED DESCRIPTION OF THE INVENTION AND PREFERRED EMBODIMENTS

Figure 1:
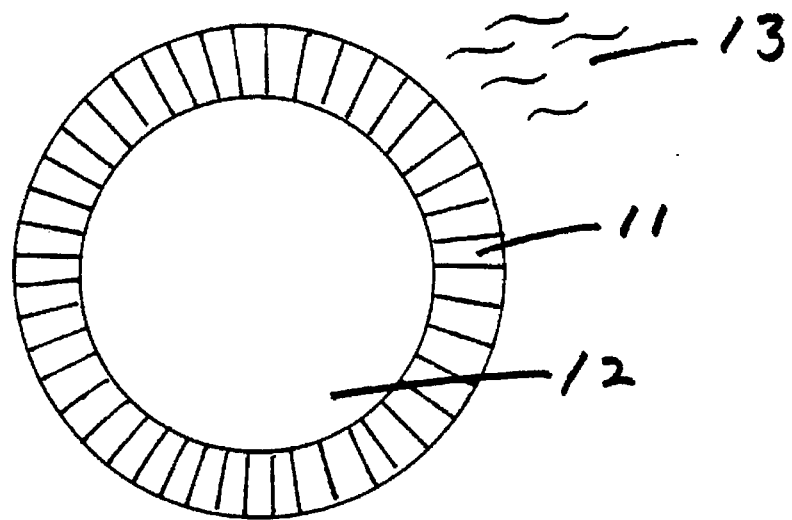
FIG. 1 is a schematic view of a pharmaceutical preparation in accordance with the invention, showing a fat particle containing dissolved cyclosporin.

The inventive pharmaceutical preparation for oral application contains a therapeutically effective quantity of one cyclosporin or of several cyclosporins, a pharmaceutically tolerable oil, 3-sn-phosphatidyl choline and, if necessary, an alkali salt of a free fatty acid. If necessary and applicable, an additional non-ionic co-emulsifier such as poly (oxyethylene)-6-glycerol-tri-(oleate, linolate) may be added.

Additionally, isotonizing substances such as glycerin and/or sorbitol and or xylitol may be contained.

The inventive pharmaceutical preparations are oil-in-water emulsions in which the individual fat droplets have a size smaller than 10 microns, preferably 5 microns, and a particle size roughly corresponding to that of the natural emulsions such as milk.

Medium-sized fat particles in the range between 0.05 and 2 microns, specifically with diameters between 0.1 and 1 micron, are particularly preferred.

Natural oils such as soy bean and/or corn oil and/or safflower oil and/or wheat germ oil and/or olive oil and/or sunflower oil and/or fish oil and/or MCT oils (medium-chain triglycerides=coconut oil) or hydrogenated or partially hydrogenated natural oils may be used as the oils; the phosphatidyl cholines are used in the form of soy lecithin or egg lecithin. The used lecithins may also be partly hydrogenated.

As cyclosporins are soluble in natural oils their simple dissolution and administration in such oils could be deemed to be evident. However, this is not sensible as the patients refuse to swallow pure fat as the oil. Moreover, this gives rise to a resorption which is by far poorer than the resorption of a preparation containing the oil in an oil-in-water emulsion.

Milk is one example of a naturally occurring oil-in-water emulsion. The addition of crystallized cyclosporin (or cyclosporin dissolved in ethanol, for instance) is an unsuccessful approach to dissolve cyclosporin(s) therein since even after vigorous stirring the predominant proportion of cyclosporin is still present in the form of undissolved crystals. This might be attributable to the fact that the cyclosporin is not able to penetrate through the lipid membrane, i.e., that it is not possible to "load" the fat droplets in such an emulsion. For this reason such an approach results in an entirely insufficient, inadequate concentration of the cyclosporin in the preparation.

It was now a surprise to find, in accordance with the invention, that it is yet very well possible to produce a form of application of cyclosporin(s) for oral administration without alcohol and without poly(oxyethylene) derivatives, in the form of a cyclosporin emulsion in natural, pharmaceutically tolerable oils, 3-sn-phosphatidyl choline and water. The used cyclosporin(s) is (are) initially dissolved in the used oil or mixture of oils, then emulsified with application of 3-sn-phosphatidyl choline, preferably in the form of soy and/or egg lecithin, and then the mixture is homogenized so as to form a stable emulsion having a particle size smaller than 10 microns, preferably between 0.05 and 2 microns on average, and most preferably in the range between 0.1 and 1 microns.

The European Patent EP-A-0 391 269 discloses oil-in-water emulsions which may contain, inter alia, cyclosporins. This pharmaceutical preparation is characterized by the aspect that it contains roughly 3 to 50% of a carrier oil consisting of an MCT oil, optionally in combination with a vegetable oil, approximately 0.05 to 20% of a phospholipid, roughly 0.03 to 10% of a non-ionic surfactant, and approximately 0.05 to 5% of an ionic surfactant. The use of ionic and non-ionic surfactants is a compulsory element in the pharmaceutical composition according to EP-A-0 391 269.

Such surfactants (detergents), however, must be absolutely avoided in the inventive pharmaceutical preparation. There is even a contra-indication on account of their toxic effects! This applies to the inventive preparations for both oral and parenteral administration.

The U.S. Pat. No. 5,206,219 discloses pharmaceutical preparations for oral administration, which contain a hydrophilic or hydrophobic surfactant. As has just been set out, however, there is a contra-indication in accordance with the present invention. Moreover, the pharmaceutical preparation according to U.S. Pat. No. 5,206,219 contains propylene glycol and/or ethylene glycol in quantities between 30 and 60%. There is a definite contra-indication on account of serious side effects in relation to the intravenous administration of these substances in accordance with the invention. Moreover, that pharmaceutical preparation contains free fatty acids in amounts of 30 to 60%, rather than natural oils.

Free fatty acids such as oleic acid, are not suitable for intravenous administration in such considerable quantities since this involves the risk of blood hemolysis.

Hence, ionic and non-ionic detergents must be avoided in accordance with the present invention. Furthermore, polyols such as propylene glycol and polyethylene glycol have to be avoided.

Whenever a sterile emulsion is desirable for oral administration it may be sterilized by heat treatment, or it may be sterilized or preserved by way of appropriate filtering and/or by means of preservatives.

The pharmaceutical preparation for the oral administration of cyclosporin(s) does not contain any objectionable adjuvants, and permits an improved and more uniform resorption.

Both natural and synthetic cyclosporins, such as the common cyclosporins A to Z, may be used as cyclosporins; cyclosporin A and cyclosporin G as well as the cyclosporin derivative SDZ IMM 125 are preferred.

The following may be used as natural oils: soy bean oil, safflower oil (safflower seed oil), coconut oils (MCT oils), fish oil, corn oil, wheat germ oil, olive oil, sunflower oil, cotton oil, walnut oil, etc. The oils may also be partly hydrogenated.

It goes without saying that the oil should be as poor as possible in peroxides and low in oxygen, in order to avoid rancidity. Antioxidants such as vitamin E or other agents, may be contained.

The used cyclosporin, e.g., cyclosporin A, is initially dissolved in the oil, e.g., corn or soy bean oil, possibly in warm condition. In this step concentrations in the range between 1 and 10 percent by weight are achieved in general.

The presence of oxygen should be carefully precluded as far as this is possible, in an attempt to prevent definitely the oil from oxidizing.

If even higher concentrations are desired additives such as poly(oxyethylene) derivatives, e.g., poly(oxyethylene)-6-glycerol tri-(oleate, linolate) and/or polyoxyethylene-40-castor oil and/or sorbitane derivatives (cf. in this context Pharm. Martindale, 28th edition, from page 376 onwards) may be added to the oil, which results in an even better solubility of the cyclosporins in the majority of cases.

It should be noted here expressis verbis, however, that these "artificial" adjuvants are not necessary in order to achieve the stable pharmaceutical preparation according to the invention.

Then water, free of oxygen as far as applicable, as well as 3-sn-phosphatidyl choline, preferably in the form of egg or soy lecithin, as the emulsifier are added to the cyclosporin-containing oily solution. In general 4 to 20 parts of the 3-sn-phosphatidyl choline are generally added to 100 parts of oil. The 3-sn-phosphatidyl choline may also be partly or completely hydrogenated.

What is preferred is egg lecithin with a 3-sn-phosphatidyl choline concentration of 50 to 85%, as well as soy lecithin having a 3-sn-phosphatidyl choline concentration of 20 to 80%. A particular advantage of the inventive pharmaceutical preparation for oral application resides in the aspect that when soy lecithin is used the addition of an alkali salt of a free fatty acid is not necessary.

Vegetable lecithins from soy beans or rape seed (colza), egg lecithin and/or lecithin derived from brain, for instance, may serve as suppliers of the 3-sn-phosphatidyl choline, the partly hydrogenated 3-sn-phosphatidyl choline or the hydrogenated 3-sn-phosphatidyl choline.

If necessary, moreover an alkali salt of a free fatty acid having 6 to 26 carbon atoms may also be added for adjusting the pH level to 5 to 9 approximately, and for facilitating the emulsification and subsequent homogenization. What is preferred here are the sodium and potassium salts of palmitic acid, palmitoleic acid, stearic acid, oleic acid, linoleic acid and linolenic acid. Even mixtures of these salts may be employed.

The mixture, which now contains cyclosporin(s), natural oil (partly or completely hydrogenated, as the case may be), 3-sn-phosphatidyl choline, water and possibly one or several alkali salts of free fatty acids is now diluted with water until the oil accounts for 5 to 80% of the total weight, preferably 20 to 50% of the total weight.

Then a crude emulsion is produced by vigorous stirring, preferably by means of an Ultra-Turrax device.

This crude emulsion is then homogenized in a high-pressure homogenizer at pressures between 100 and 500 bar, possibly several times, until an emulsion is obtained wherein the particle size of all particles is less than 20 microns, preferably 10 microns and most preferably less than 5 microns. The fat particles present an average size of 0.05 to 10 microns, preferably between 0.05 and 2 microns and most preferably between 0.1 and 1 micron. The employed high-pressure homogenizer should preferably comprise three pistons.

If necessary, water is then added so as to dilute the emulsion to the desired concentration. Subsequently, the emulsion may be filled in the suitable forms of administration, e.g., in vials and/or ampoules for drinking or also in soft-gelatin capsules.

For a protection of the drug form for oral administration from decomposition by bacteria thermo-sterilization may be carded out, if desired, and/or the drug form is protected by the addition of common preservatives such as benzoic acid, sorbic acid, p-hydroxy benzoic ester, etc.

It is common and preferable to produce the cyclosporin contained in the drug form for oral application in a completely dissolved form. In such a case, the cyclosporin, dissolved in the oil, is contained inside a fat particle, while the oil is enclosed by an envelope consisting substantially of phospholipid (3-sn-phosphatidyl choline).

FIG. 1 is a schematic illustration of the structure of the fat particles containing cyclosporin in accordance with the present invention. This Figure shows the envelope 11 of the particle (comprised of the phospholipid 3-sn-phosphatidyl choline), the cyclosporin dissolved in oil 12 inside the envelope, and water 13 surrounding the envelope.

It is even possible, too, however, to use the cyclosporin in production in a concentration so high that the finally obtained finished drug form for oral application only one part of the cyclosporin is present in a dissolved form while another part is enclosed in solid form inside the fat particle. This is achieved in a way that the cyclosporin is dissolved in the oil at an elevated temperature (e.g., 50° to 80° C.) and thus a solution is produced which is oversaturated with cyclosporin at room temperature. Then the emulsifying and homogenizing steps are carried out at an elevated temperature. Following its preparation the emulsion is then cooled down to room temperature, with crystallization of part of the cyclosporin contained inside the fat particles. On account of the envelope enclosing the fat particle, which cannot be penetrated by the solid cyclosporin, the cyclosporin remains enclosed.

Figure 2:
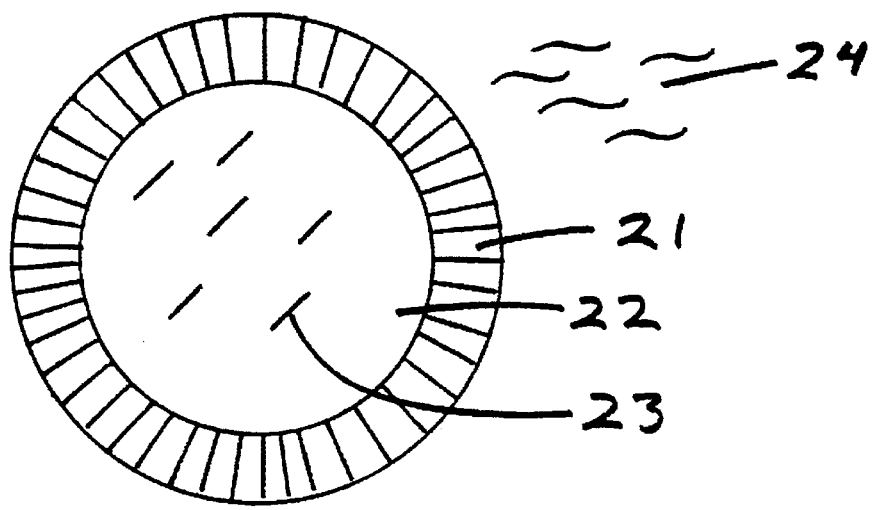
FIG. 2 is a schematic view of a pharmaceutical preparation in accordance with the invention, showing a fat particle containing dissolved as well as crystalline cyclosporin.

FIG. 2 is a schematic view of such a fat particle. This Figure shows the envelope 21 of the particle (comprised of the phospholipid 3-sn-phosphatidyl choline), the cyclosporin dissolved in oil 22 inside the envelope, the cyclosporing microcrystals 23 inside the envelope, and water 24 surrounding the envelope.

The emulsion may be administered per os in the form of drinking ampoules, drops, soft-gelatin capsules. The fat particles with the cyclosporin enclosed therein is then digested in the gastrointestinal tract by the enzymes supplied there, so that the cyclosporin is released. As the fat particles, which are comparable to milk as a natural fat emulsion, are affected in the stomach to a minor extent only the active substance is mainly released in the small intestines where the fat particles are broken down in a natural manner under the action of the pancreatin contained there, so as to release the cyclosporin. With these provisions an improved resorption is achieved, along with a more uniform and more reliable intake into the organism.

The following examples as embodiments describe details of the inventive pharmaceutical preparation and of the process for producing same. However, the invention is not restricted thereto.

EXAMPLE 1

10 kg of winterized soy bean oil (neutral pH value, free of peroxides) is gassed with nitrogen and heated to about 50° C. (The term "winterized soy bean oil" is understood to denote soy bean oil cooled to a temperature below −10° C. prior to application so as to precipitate insoluble components which are filtered out.) Then 400 g of cyclosporin A are added to this soy bean oil and dissolved while being stirred.

13.8 kg of water are charged into a second vessel and gassed with nitrogen. Then 1.2 kg of egg lecithin presenting a phosphatidyl choline concentration of roughly 70% (and approximately 18% of phosphatidyl ethanolamine) as well as 50 g of sodium oleate are added. While vigorously stirring by means of an Ultra-Turrax device, a crude emulsion is produced at a temperature of roughly 50° C.

Then the soy bean oil with the cyclosporin A dissolved therein is added, and stirring with the Ultra-Turrax device is continued for 5 minutes approximately.

The crude emulsion so produced is homogenized at 100 to 500 bar in a high-pressure homogenizer. The homogenizing operation is repeated until the desired fat particle size is reached. At each homogenizing operation the mean droplet size is reduced. At the end of four homogenization steps a mean droplet size of 0.2 to 0.6 microns is achieved.

After each homogenization step the emulsion should be cooled down to a level of roughly 30° to 60° C.

The distribution of particle sizes of the fat particles containing the cyclosporin is as follows:

| Particle Size (microns) | Percentage of Particles |
| --- | --- |
| <0.2 | 15 |
| 0.2 to 0.5 | 56 |
| 0.5 to 0.9 | 19 |
| 0.9 to 1.2 | 6 |
| 1.2 to 1.5 | 2 |
| 1.5 to 1.9 | <1 |
| 1.9 to 2.2 | <1 |
| 2.2 to 3.2 | <1 |
| >3.2 | 0 |

Approximately 25 kg of an emulsion are yielded which contains a total of 400 g cyclosporin A. This means that 100 mg cyclosporin are contained in 6 mL of the emulsion.

Flavoring substances may be added so that the emulsion will have an agreeable taste when it is administered.

The emulsion is filled into drinking ampoules of 10 mL each and subject to thermal sterilization in the usual manner.

EXAMPLE 2

The process of Example 1 is repeated, using a fish oil concentrate instead of the soy bean oil, which contains 18% of eicosapentaenoic acid and 12% of docosahexaenoic acid.

EXAMPLE 3

Example 1 is repeated, using a soy lecithin instead of the egg lecithin used in Example 1, which contains a 60% proportion of 3-sn-phosphatidyl choline.

EXAMPLE 4

Example 1 is repeated, using a partly hydrogenated egg lecithin with approximately 80% of partly hydrogenated 3-sn-phosphatidyl choline, instead of the egg lecithin.

EXAMPLE 5

10 kg of soy bean oil having a free fatty acid concentration of 2.5 meq/1 and presenting a pH level of 3.5 to 4.5 is heated to 50° C. approximately, whereupon 500 g of cyclosporin A are added. In correspondence with Example 1 a crude emulsion is produced while stirring in an Ultra-Turrax device. Then a 10% sodium hydroxide solution is added to adjust a pH level of 6.5 to 8.5. The production process then continues in correspondence with Example 1.

EXAMPLE 6

Example 2 is repeated, but with 250 g cyclosporin A and 250 g cyclosporin G instead of the 400 g cyclosporin A.

EXAMPLE 7

A pharmaceutical preparation containing cyclosporin is produced as described in Example 1, substituting, however, the cyclosporin A by 150 g of SDZ IMM 125, a hydroxyethyl derivative of D-serine-8-cyclosporin. The production and the structure of SDZ IMM 125 are described in G. Baumann et al., Transplantation Proceedings, vol. 24, No. 4, Suppl. 2, pages 31 to 38 (1992).

EXAMPLE 8

This example illustrates the release of cyclosporin from the inventive pharmaceutical preparation in vitro.

(a) 10 mL of the pharmaceutical preparation according to Example 1 are introduced into 50 mL of synthetic gastric juice according to USP XXII, containing hydrochloric acid, sodium chloride and pepsin, having a pH level of 1.2, whereupon stirring continues for 2 hours at 37° C. The emulsion remains practically unchanged.

(b) 10 mL of the pharmaceutical preparation according to Example 1 are introduced into 50 mL of synthetic gastric juice according to USP XXII, containing pancreatin and presenting a pH level of 7.5; stirring then continues for 1 hour at 37° C. The emulsion does not remain stable; the fat particles are rather decomposed and release the cyclosporin therefrom.

For parenteral administration the following pharmaceutical composition is preferably applied:

1. Soy bean oil—up to 400 g/L
2. Egg lecithin—5 to 20 g/L, the egg lecithin required to contain 60% to 85% of phosphatidyl choline
3. Sodium salt or potassium salt of a fatty acid having at least 10 carbon atoms—0.2 to 1.0 g/L. It is also possible to use an alkali lye plus fatty acid instead of the salt plus fatty acid.

What is claimed is:

1. A process for the production of a pharmaceutical preparation for oral administration, said process comprising:
   (a) dissolving (i) at least one cyclosporine selected from the group consisting of natural cyclosporines, synthetic cyclosporines, and semi-synthetic cyclosporine derivatives, in (ii) at least one natural oil, essentially free of peroxides, to form a solution wherein said cyclosporine is dissolved in said natural oil; and
   (b) emulsifying said solution with (iii) water and (iv) pharmaceutically tolerable alkali salts of free fatty acids and (v) at least one member selected from the group consisting of 3-sn-phosphatidyl choline, phosphatidyl ethanol amine, egg lecithin containing 3-sn-phosphatidyl choline, brain-derived lecithin containing 3-sn-phosphatidyl choline, vegetable lecithin containing 3-sn-phosphatidyl choline, and at least partially hydrogenated forms thereof, to enclose said natural oil in the interior of fatty particles in which essentially all of component (ii) is surrounded by an envelope of component (v), said fatty acid particles being emulsified in water, said pharmaceutical preparation being essentially free of poly(oxyethylene)-40-castor oil, ethanol, and ionic and non-ionic surfactants.

2. A process according to claim 1, wherein step (a) is completely performed prior to step (b), and step (b) is performed by
   (i) emulsifying said solution in water to a crude emulsion to form a mixture, and
   (ii) homogenizing said mixture to an emulsion, with a particle size of less than 10 μm.

3. A process according to claim 2, wherein in step (b) (ii) said particle size is less than 2 microns.

4. A process according to claim 1, wherein step (b) comprises emulsifying said solution with water and at least one member of component (v), said process further comprising forming, prior to step (b), a mixture containing said solution of step (a), said water, said at least one member of component (v), and 0.01 to 0.15% of a member selected from the group consisting of pharmaceutically acceptable alkali salts of free natural fatty acids, and further prior to step (b), adjusting said mixture to a pH value of 5 to 10, by means of alkali lye(s).

5. A process according to claim 1, further comprising adjusting said emulsion to a pH value of 5 to 10 with a member selected from the group consisting of fatty acids and pharmaceutically acceptable alkali salts thereof.

6. A process according to claim 5 wherein said pH value is adjusted to 7 to 9.

7. A process according to claim 1, wherein all substances used are substantially oxygen-free.

8. A process according to claim 1, wherein step (b) comprises
   (i) forming a crude emulsion by means of thorough stirring, and
   (ii) further emulsifying said crude emulsion in a high-pressure homogenizer at pressures between 100 and 500 bar.

9. A process according to claim 8, wherein said high-pressure homogenizer comprises at least three pistons.

10. A method for administering a cyclosporine to a subject in need thereof, said method comprising orally administering to said subject a pharmaceutical preparation comprising:
    (a) at least one cyclosporine selected from the group consisting of natural cyclosporines, synthetic cyclosporines, and semi-synthetic cyclosporine derivatives,
    (b) at least one natural oil of natural origin, essentially free of peroxides,
    (c) at least one member selected from the group consisting of 3-sn-phosphatidyl choline, phosphatidyl ethanol amine, egg lecithin containing 3-sn-phosphatidyl choline, brain-derived lecithin containing 3-sn-phosphatidyl choline, vegetable lecithin containing 3-sn-phosphatidyl choline, and at least partially hydrogenated forms thereof,
    (d) pharmaceutically tolerable alkali salts of free fatty acids, and
    (e) water, wherein component (a) is dissolved in component (b) and component (b) is enclosed in the interior of fatty particles in which component (b) is surrounded by an envelope of component (c), said fatty particles being emulsified in water, the pharmaceutical preparation being essentially free of poly(oxyethylene)-40-castor oil, ethanol and
    ionic and non-ionic surfactants.

* * * * *